(12) United States Patent
Duan et al.

(10) Patent No.: US 11,579,029 B2
(45) Date of Patent: Feb. 14, 2023

(54) CAPSULE DEVICE FOR PRESSURE MEASURING

(71) Applicants: Ankon Medical Technologies (Shanghai) Co., LTD., Shanghai (CN); Anx IP Holding PTE. LTD., Singapore (SG)

(72) Inventors: Xiaodong Duan, Pleasanton, CA (US); Shaobang Zhang, Shanghai (CN); Lei Liu, Suzhou (CN)

(73) Assignees: ANKON MEDICAL TECHNOLOGIES (SHANGHAI) CO., LTD., Shanghai (CN); ANX IP HOLDING PTE. LTD., Singapore (SG)

( * ) Notice: Subject to any disclaimer, the term of this patent is extended or adjusted under 35 U.S.C. 154(b) by 231 days.

(21) Appl. No.: 17/187,190

(22) Filed: Feb. 26, 2021

(65) Prior Publication Data
US 2021/0262872 A1    Aug. 26, 2021

(30) Foreign Application Priority Data
Feb. 26, 2020    (CN) .......................... 202010121181.9

(51) Int. Cl.
| A61B 1/01 | (2006.01) |
| G01L 1/22 | (2006.01) |
| A61B 1/00 | (2006.01) |
| A61B 1/04 | (2006.01) |
| A61B 5/03 | (2006.01) |

(52) U.S. Cl.
CPC ........ *G01L 1/2287* (2013.01); *A61B 1/00018* (2013.01); *A61B 1/041* (2013.01); *A61B 5/036* (2013.01); *G01L 1/225* (2013.01)

(58) Field of Classification Search
CPC ..... A61B 5/036; A61B 1/041; A61B 1/00018; G01L 1/225; G01L 1/2287
See application file for complete search history.

(56) References Cited

FOREIGN PATENT DOCUMENTS

| CN | 102138794 A | * | 8/2011 |
| CN | 104706307 A | * | 6/2015 |

\* cited by examiner

*Primary Examiner* — Jamel E Williams
(74) *Attorney, Agent, or Firm* — Treasure IP Group, LLC

(57) ABSTRACT

The present invention discloses a capsule device for pressure measurement. The capsule device comprises a capsule enclosure, a data transmission assembly and a thin film pressure sensor. The capsule enclosure is formed with an accommodating chamber, and the data transmission assembly is arranged in the accommodating chamber. The thin film pressure sensor is attached to the outer surface of the capsule enclosure to measure pressure, and the thin film pressure sensor is connected with the data transmission assembly.

16 Claims, 8 Drawing Sheets

CAPSULE DEVICE FOR PRESSURE MEASURING

CROSS-REFERENCE OF RELATED APPLICATIONS

The application claims priority to Chinese Patent Application No. 202010121181.9 filed on Feb. 26, 2021, the contents of which are incorporated by reference herein.

FIELD OF INVENTION

The present invention relates to the art of pressure measurement, and more particularly to a capsule device for pressure measuring with a thin film pressure sensor.

BACKGROUND

Existing capsule devices used to measure the pressure of digestive tract, uterus or vagina generally measure pressure using MEMS (Micro-Electro-Mechanical System) sensors. MEMS sensors require secondary encapsulation to meet biocompatibility requirements. However, secondary encapsulation has an impact on the output range and accuracy of the sensor, so the process procedures are complicated. In addition, the MEMS sensor is usually installed inside a capsule device, making the size larger, which is not conducive to miniaturization of the capsule device.

SUMMARY OF THE INVENTION

The present invention discloses a capsule device with simple process and small size.

In order to achieve the above objectives, the present invention specifically adopts the following technical solutions:

The present invention discloses a capsule device, comprises a capsule enclosure, a data transmission assembly and a thin film pressure sensor. The capsule enclosure is formed with an accommodating chamber, the data transmission assembly is arranged in the accommodating chamber. The thin film pressure sensor is attached to the outer surface of the capsule enclosure to measure pressure, and the thin film pressure sensor is connected with the data transmission assembly.

Preferably, the capsule enclosure comprises a cylindrical side wall, and the thin film pressure sensor is attached to the outer surface of the side wall along the circumferential direction of the side wall.

Preferably, the capsule device further comprises a first vent passage. One end of the first vent passage is connected to the thin film pressure sensor, and the other end of the first vent passage is connected to the accommodating chamber.

Preferably, the capsule device further comprises a signal line. One end of the signal line is connected to the thin film pressure sensor, and the other end of the signal line is connected to the data transmission assembly.

Preferably, the signal line passes through the first vent passage.

Preferably, the first vent passage is arranged between the thin film pressure sensor and the capsule enclosure. The capsule enclosure is arranged with an opening, and the first vent passage is connected to the accommodating chamber via the opening.

Preferably, one or more thin film pressure sensors are attached to the outer surface of the capsule enclosure.

Preferably, the thin film pressure sensor comprises a circuit layer, a bonding layer and a functional film layer. The circuit layer and the functional film layer are bonded together through the bonding layer, and the circuit layer is attached to the outer surface of the capsule enclosure.

Preferably, the circuit layer comprises a thin film, one or more sensing elements are arranged on the thin film, and one end of the signal line is connected to the sensing elements.

Preferably, a plurality of sensing elements are arranged on the thin film of the circuit layer. The sensing elements are arranged in an array, and the sensing elements in each row are connected in series and connected to the accommodating chamber through the signal line.

Preferably, the bonding layer is provided with a first through hole to form a cavity between the circuit layer and the functional film layer. The cavity exposes all the sensing elements within the contact range of the functional film layer, and forms an air passage between the sensing element and the accommodating chamber.

Preferably, the first through hole comprises a hole and a second vent passage. The hole is arranged corresponding to the sensing element, and the sensing element is arranged in the hole. One end of the second vent passage is connected to the hole, and the other end of the second vent passage is connected to the vent hole in the circuit layer.

Preferably, the functional film layer comprises an iontronic film and a thin film, and the thin film is made of a biocompatible material.

Preferably, the functional film layer is of cantilever type. A waterproof layer is arranged outside the cantilever type functional film layer, and the waterproof layer is sealed and bonded to the cantilever type functional film layer.

Preferably, the cantilever type functional film layer is provided with a cantilever unit corresponding to the position of each sensing element, and the cantilever unit is cut in a functional film layer of a preset shape, so that the functional film layer forms a cantilever structure.

Preferably, the functional film layer is of cantilever beam type. A waterproof layer is arranged outside the cantilever beam type functional film layer, and the waterproof layer is sealed and bonded to the cantilever beam type functional film layer.

Preferably, the cantilever beam type functional film layer is provided with a cantilever beam assembly corresponding to the position of each sensing element, and the cantilever beam assembly is cut in a functional film layer of a preset shape, so that the functional film layer forms a cantilever beam structure.

Preferably, the capsule device further comprises an image acquisition assembly arranged in the accommodating chamber.

Compared with the prior art, the thin film pressure sensor of the present invention can meet the biocompatibility requirements without secondary encapsulation, its process is simple. The thin film pressure sensor is attached to the outer surface of the capsule enclosure and does not take up the space inside the capsule enclosure, so the capsule enclosure can be made smaller, and the thin film pressure sensor itself is relatively thin, it takes up little space outside the capsule enclosure, so the overall size of the capsule device can be made smaller.

Figure 1:
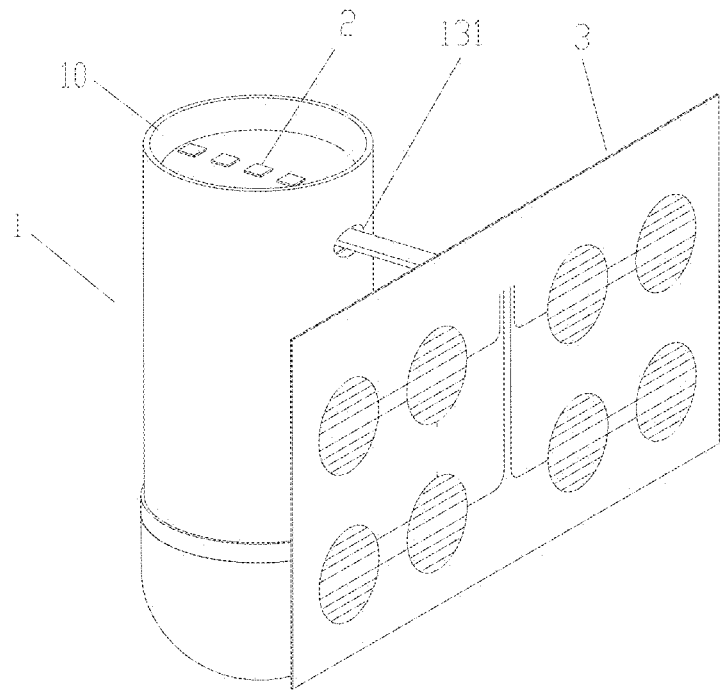
FIG. 1 is an exploded view of an embodiment of a capsule device for pressure measuring, in accordance with aspects of the present invention.

Elements in the drawings are: 1. Capsule enclosure; 10. Accommodating chamber; 11. First end; 12. Second end; 13. Side wall; 131. Opening; 2. Data transmission assembly; 21. Antenna; 22. Data collection and processing module; 23. Battery; 3. Thin film pressure sensor; 31. Connecting member; 311. Second through hole; 32. Circuit layer; 321. Thin film; 3211. Hole; 3212. Second vent passage; 3213. Vent hole; 322. Sensing element; 33. Bonding layer; 331. First through hole; 34. Functional film layer; 35. Waterproof layer; 4. First vent passage; 5. Signal line; 6. Image acquisition assembly; 61. Camera; 62. Illuminating unit; 63. Image sensor; 7. Capsule tether; 71. Suction cup; 72. Vent tube; 8. Syringe; 100. Capsule device for pressure measuring; 200. Digestive tract wall.

DETAILED DESCRIPTION

In order to make the objects, technical solutions, and advantages of the present invention more understandable, the present invention can be further described in detail below with reference to the accompanying drawings and embodiments. It is understood that the embodiments described herein are merely illustrative of the invention and are not construed as limited to the invention.

Figure 2:
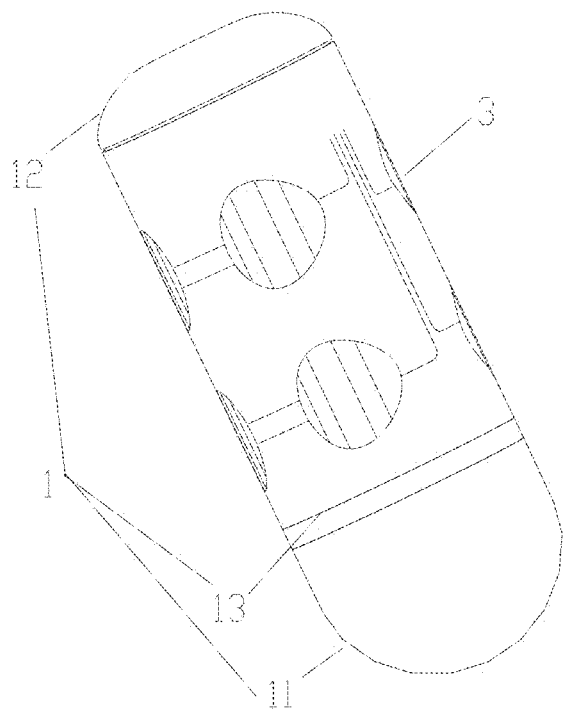
FIG. 2 is a schematic view of an embodiment of the capsule device for pressure measuring, in accordance with aspects of the present invention.

Referring to FIG. 1 and FIG. 2, the present invention discloses a capsule device for pressure measuring 100, the capsule device 100 comprises a capsule enclosure 1, a data transmission assembly 2 and a thin film pressure sensor 3. The capsule enclosure 1 is formed with an accommodating chamber 10, a data transmission assembly 2 is arranged in the accommodating chamber 10. The thin film pressure sensor 3 is attached to the outer surface of the capsule enclosure 1 to measure pressure; and the thin film pressure sensor 3 is connected with the data transmission assembly 2.

In the embodiments of the present invention, the thin film pressure sensor 3 is attached to the outer surface of the capsule enclosure 1 (by means of gluing, for example), and compared with the traditional MEMS sensor, the thin film pressure sensor of the present invention can meet the biocompatibility requirements without secondary encapsulation, its process procedure is simple. Further, since the thin film pressure sensor 3 is attached to the outer surface of the capsule enclosure 1 and does not take up the space inside the capsule enclosure 1, the capsule enclosure 1 can be made smaller, and the thin film pressure sensor 3 itself is relatively thin, it takes up very little space outside the capsule enclosure 1, so the overall size of the capsule device can be made smaller.

The capsule enclosure 1 comprises a first end 11, a second end 12, and a cylindrical side wall 13. The first end 11 and the second end 12 are respectively disposed at two ends of the side wall 13, so as to jointly form an accommodating chamber 10. The thin film pressure sensor 3 is attached to the outer surface of the side wall 13 along the circumferential direction of the side wall 13.

When measuring the pressure of a subject, the capsule device is put into the subject, so that the direct muscle pressure in different positions on the tube wall of the subject, the gas pressure and fluid pressure in a cavity of the subject act on the thin film pressure sensor 3 to convert the capacitance of sensing element in the thin film pressure sensor 3 into pressure information, and the pressure information is transmitted to an external device through the data transmission assembly 2 to obtain the pressure value of the subject. Specifically, in an embodiment of the present application, the subject is a digestive tract. It can be understood that the subject may also be a uterus, vagina, rectum, or female urethra. The existing capsule device for pressure measuring has a MEMS sensor placed at the head or tail of the capsule enclosure. In the esophagus, intestine and other tubular parts that are generally coaxial with the capsule device, the force can act on the cylindrical surface of the capsule enclosure when the muscles of the subject are contracted. The pressure can be distorted when the pressure of the subject is measured as the muscles are covering the cylindrical surface of the capsule enclosure but not completely covering its two ends. In the present invention, the thin film pressure sensor 3 is attached to the outer surface of the side wall 13 along the circumferential direction of the side wall 13, so that in the esophagus, intestine, and other tubular parts that are coaxial with the capsule enclosure, the force can act on the cylindrical surface of the capsule enclosure when the muscles of the subject are contracted, that is, the muscles of the subject are covering the thin film pressure sensor 3, so that the measured pressure value in the subject is more accurate.

Figure 9:
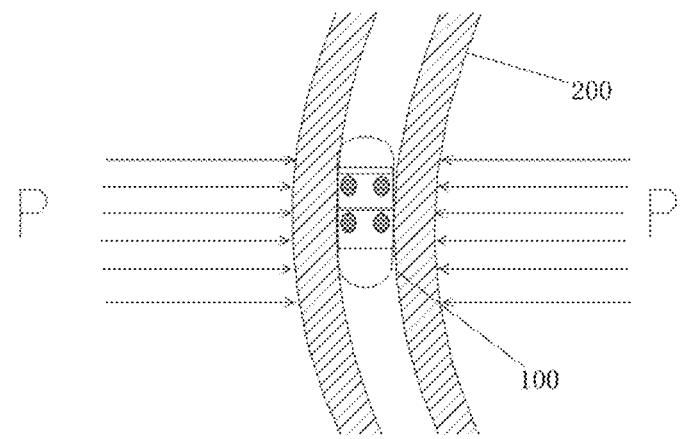
FIGS. 9-12 illustrate the states of the capsule device in various positions in a subject.
Figure 10:
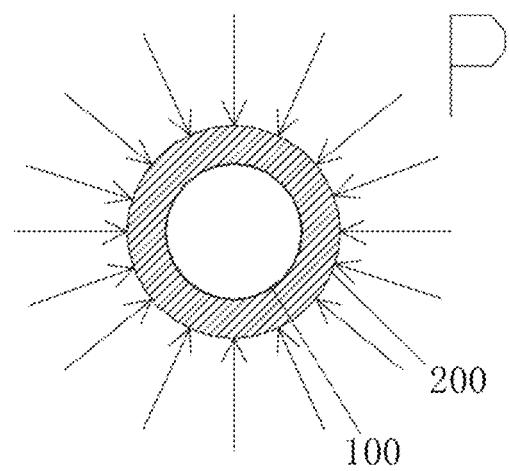
Figure 11:
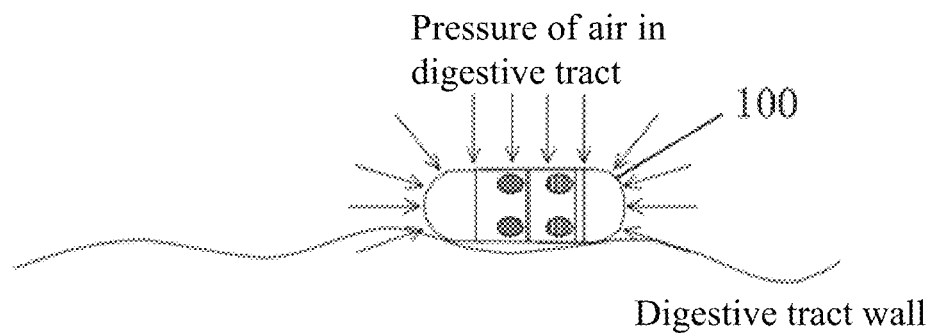
Figure 12:
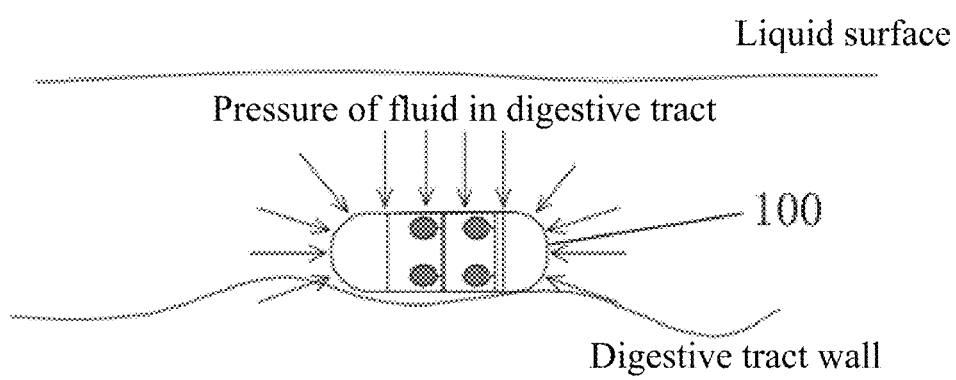

Referring to FIGS. 9-12 illustrate the states of the capsule device in various positions in the subject. In FIGS. 9-10, the direct muscle pressure of the digestive tract wall 200 of the subject acts on the thin film pressure sensor 3 of the capsule device 100. In FIG. 11, the pressure of air in the digestive tract of the subject acts on the thin film pressure sensor 3 of the capsule device 100. In FIG. 12, the pressure of fluid in the digestive tract of the subject acts on the thin film pressure sensor 3 of the capsule device 100.

It can be understood that in other embodiments of the present application, the thin film pressure sensor 3 may also be attached to the outside of the side wall 13 in a non-circumferential direction.

It can be understood that one or more thin film pressure sensors 3 can be attached to the side wall of the capsule enclosure 1. In the following, a thin film pressure sensor 3 can be used as an example to introduce.

Figure 3:
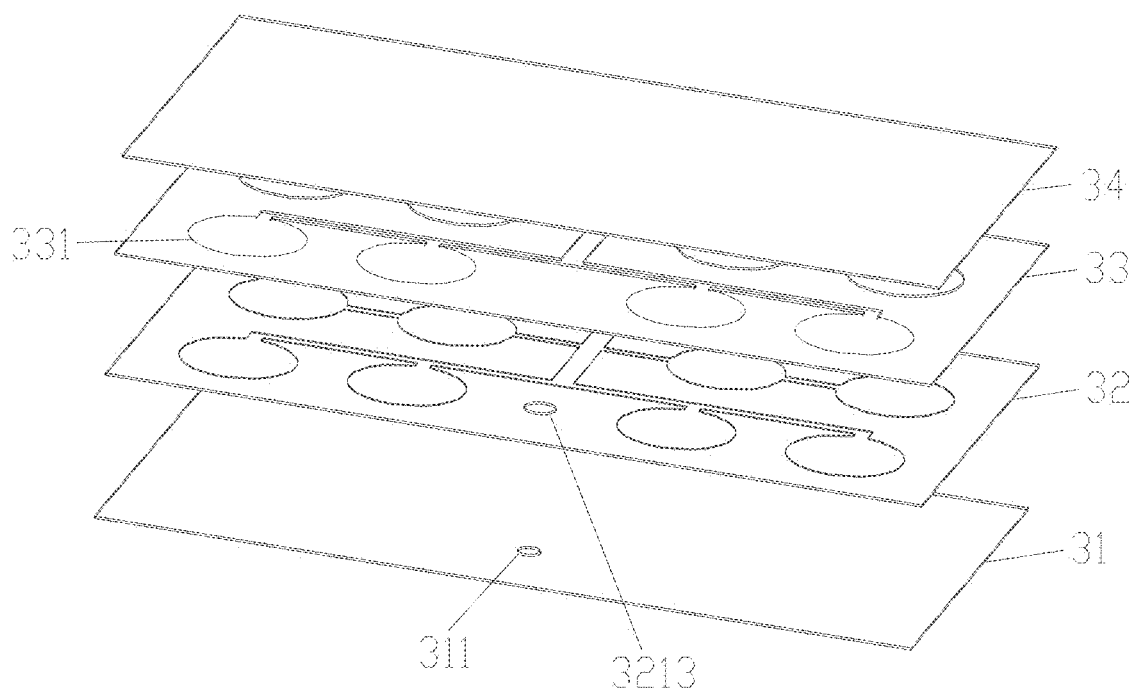
FIG. 3 is an exploded view of a first exemplar embodiment of a thin film pressure sensor, in accordance with aspects of the present invention.
Figure 4:
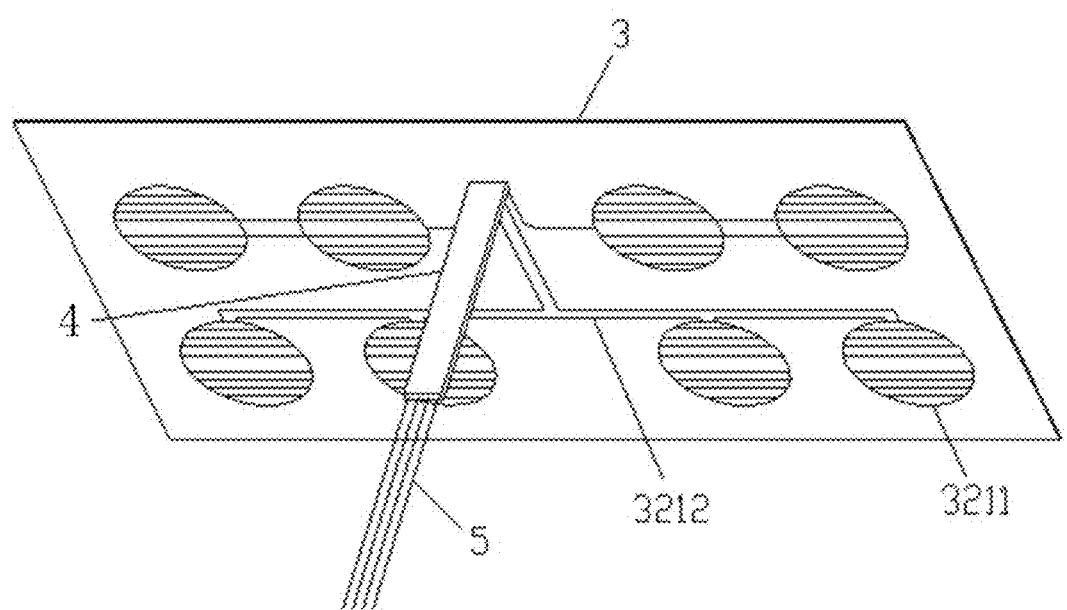
FIG. 4 is a structural view of a first exemplar embodiment of the thin film pressure sensor, in accordance with aspects of the present invention.
Figure 5:
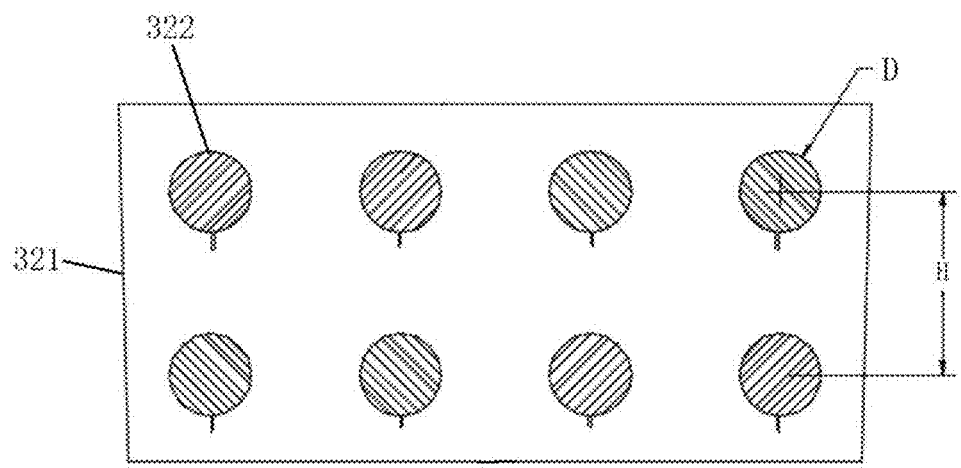
FIG. 5 is a structural view of a first exemplar embodiment of a circuit layer, in accordance with aspects of the present invention.

Referring to FIGS. 3-5, corresponding to the thin film pressure sensor 3 in the first embodiment. The thin film pressure sensor 3 comprises a circuit layer 32, a bonding layer 33 and a functional film layer 34. The circuit layer 32, the bonding layer 33 and the functional film layer 34 are stacked in sequence, and the outer surface of the circuit layer 32 is fixedly attached to the outer surface of the side wall 13 through a connecting member 31. In a specific embodiment, the connecting member 31 may be a colloid, made of a biocompatible material, and the colloid is completely attached to the back of the thin film pressure sensor 3. The bonding layer 33 is a double-sided colloid for bonding the circuit layer 32 and the functional film layer 34 into one. The material of the colloid can be, but is not limited to, transparent silicone, TPU (thermoplastic urethanes), PET (polyethylene terephthalate). The functional film layer 34 consists of an iontronic film, the iontronic film is uniformly coated on a thin film and cured to form the functional film layer 34. The coating method includes brushing, spin coating, dipping, spraying, etc. The thin film is made of waterproof biocompatible materials, for example, it can be made of the following materials: PET, PU (polyurethane), PI (polyimide), PVC (polyvinyl chloride), PVDC (poly (vinylidene chloride)) etc. In the embodiment, it is preferable to coat an iontronic film on the PET film to form the functional film layer 34. In the embodiment, the thickness of the functional film layer 34 is 50 um (micrometers), the thickness of the bonding layer 33 is 30 um, the thickness of the circuit layer 32 is 50 um, and the thickness of the connecting member 31 is 30 um.

Referring to FIGS. 3-5, the circuit layer 32 comprises a thin film 321 on which one or more sensing elements 322 are arranged, and each sensing element 322 comprises an even number of electrodes. In one embodiment, the sensing element 322 is printed on the thin film 321 through a printed circuit process (as shown in FIG. 5). The shape of the sensing element 322 can be set as required, such as a circle, a triangle, a square, a pentagon, an ellipse, etc., and a circle is taken as an example in the present invention. The sensing elements 322 are connected to the accommodating chamber 10 through a signal line 5. Each sensing element 322 is connected to the accommodating chamber 10 through its separate signal line 5, or a plurality of sensing elements 322 are connected in series to the accommodating chamber 10 through a common signal line 5. Preferably, a plurality of sensing elements 322 are arranged in an array on the thin film 321, the sensing elements 322 in each row are connected in series to serve as a total sensing element and each total sensing element is connected to the accommodating chamber 10 through a signal line 5. Such connection method can be used to measure the peristaltic velocity of intestine. As shown in FIG. 5, the thin film 321 is arranged with eight sensing elements 322. The four sensing elements 322 in the first row are connected in series to the accommodating chamber 10 through a common signal line 5, and the four sensing elements 322 in the second row are also connected in series to the accommodating chamber 10 through a common signal line 5.

When the plurality of sensing elements 322 are arranged in an array, the array pitch H of the sensing elements 322 is 5 cm-15 cm. The diameter D of the sensing elements 322 is 3 mm-6 mm. Since the length of the cylindrical surface of the capsule enclosure 1 is limited, the array pitch H of the sensing elements 322 is set to 5 cm-15 cm to make full use of the cylindrical surface area of the capsule enclosure 1. When the diameter D of the sensing element 322 is 3 mm, more sensing elements 322 can be arranged on the unit circumference of the thin film pressure sensor, thereby increasing the sampling points and improving the accuracy. When the diameter D of the sensing element 322 is 6 mm, the thin film pressure sensor has a high sensitivity, but there are less sensing elements 322 that can be arranged per unit circumference. Therefore, the sensing element 322 with a diameter D of 3 mm-6 mm can ensure measuring accuracy and sensitivity. In actual design, the area of cylindrical surface of the capsule enclosure 1 can be adjusted to actual needs.

The bonding layer 33 is provided with a first through hole 331 to form a cavity between the circuit layer 32 and the functional film layer 34. The cavity formed by the first through hole 331 can expose all the sensing elements 322 within the contact range of the functional film layer 34, so that the functional film layer 34 can fully contact the sensing elements 322 of the circuit layer 32 when subjected to external pressure. Also, the first through hole 331 forms an air passage between all the sensing elements 322 and the accommodating chamber 10. FIG. 4 shows a specific example of the first through hole 331. Referring to FIGS. 4 and 5, the side wall 13 of the capsule device of the present invention is arranged with an opening 131, and the signal line 5 is connected to the thin film pressure sensor 3 through the opening 131. The bonding layer 33 is arranged with a first through hole 331. The first through hole 331 comprises a hole 3211 and a second vent passage 3212. The thin film 321 is arranged with a vent hole 3213. The hole 3211 is arranged corresponding to the sensing element 322. The sensing elements 322 are housed in the holes 3211 in a one-to-one correspondence, so that the functional film layer 34 can fully contact the sensing elements 322 when subjected to external pressure. One end of the second vent passage 3212 is connected to each hole 3211 respectively, and the other end of the second vent passage 3212 is connected to the vent hole 3213. Specifically, the second vent passage 3212 is formed by perforating the bonding layer 33 by a cutting die. The connecting member 31 is arranged with a second through hole 311. The second through hole 311 corresponds to the vent hole 3213. One end of the first vent passage 4 is hermetically connected to the vent hole 3213 through the second through hole 311 in a sealed manner, and the other end of the first vent passage 4 is connected to the opening 131 in a sealed manner. The first vent passage 4 is connected to the accommodating chamber 10 through the vent hole 3213, the second through hole 311 and the opening 131, thus to directly form a gas passage between the thin film pressure sensor 3 and the accommodating chamber 10. The sensing elements 322 are respectively disposed in the holes 3211, the signal line 5 passes through the first vent passage 4. One end of the signal line 5 is connected to each sensing element 322, and the other end of the signal line 5 is connected to the data transmission assembly 2. In the embodiment, the signal line 5 of the circuit layer 32 can be directly welded to the welding point of the data transmission assembly 2 or connected to the data transmission assembly 2 through a connector. Therefore, the thin film pressure sensor 3 can communicate with the data transmission assembly 2 arranged in the accommodating chamber 10 through the signal line 5, and the air pressure in the hole 3211 can also be discharged through the first vent passage 4.

In the embodiment, the signal line 5 is made of silver material, and the signal line located in the second vent passage 3212 is disposed by printing in the second vent passage 3212. It can be understood that the signal line can also be made of other conductive materials, such as copper. The signal line 5 can also be disposed in the second vent passage 3212 by other processes, such as spraying.

In the embodiment, eight holes 3211 are cut in the bonding layer 33, and the eight holes 3211 are distributed in two rows and four columns. The holes 3211 in the first column are connected to the holes 3211 in the second column, and the holes 3211 in the fourth column are connected to the holes 3211 in the third column. Four second vent passages 3212 are designed and arranged between two adjacent rows of holes 3211 in the middle. One ends of the four second vent passages 3212 are respectively connected to the four holes 3211 in the middle, and the other ends of the second vent passages 3212 are connected to the vent hole 3213. It can be understood that, in other embodiments, the second vent passages 3212 may also be directly connected to each hole 3211 respectively.

In the embodiment, only one vent hole 3213 is provided, and each second vent passage 3212 is connected to the vent hole 3213.

In the embodiment, only one vent hole 3213 is provided, and correspondingly, only one second through hole 311 is provided, and each second vent passage 3212 is connected to the vent hole 3213, so that there is only one connection channel between the thin film pressure sensor 3 and the side wall 13, making the connection between the thin film pressure sensor 3 and the side wall 13 simple.

It can be understood that in other embodiments, a plurality of vent holes 3213 are provided, and correspondingly, a plurality of second through holes 311 are provided. Each second vent passage 3212 is connected to a vent hole 3213.

In the present invention, the two ends of the first vent passage 4 are respectively connected to the second through hole 311 and the opening 131 in a sealed manner, and the signal line 5 is inserted into the first vent passage 4, which is not only convenient for reducing air pressure in the holes 3211 to prevent too high air pressure therein, and also protecting the signal line 5 from being affected by moisture in the subject.

When a plurality of thin film pressure sensors 3 are disposed on the side wall of the capsule enclosure 1, the thin film pressure sensors 3 can be connected to the accommodating chamber 10 through the same opening 131 or different openings 131.

It can be understood that in other embodiments, the signal line 5 can also be placed outside the first vent passage 4. With this structure, the signal line 5 cannot affect the venting effect of the first vent passage 4. In order to protect the signal line 5 from being affected by moisture, a protection tube can be additionally provided, and the signal line 5 is arranged in the protection tube.

To sum up, the combination of the circuit layer 32, the bonding layer 33 and the functional film layer 34 forms a capacitor. When the functional film layer 34 is subjected to an external pressure, a change of the external pressure can make the volume of the cavity in the circuit layer 32 and the functional film layer 34 change, so that the functional film layer 34 deforms toward the circuit layer 32, and the iontronic film of the functional film layer 34 contacts the sensing element 322 of the circuit layer 32, resulting in a change in the capacitance value of the sensing element 322. Further, the correspondence between the capacitance value and the external pressure can be calibrated to indicate the magnitude of pressure. When the external pressure disappears, the functional film layer 34 can be restored to its original state. So, a plurality of measurements are allowed. The iontronic film of the functional film layer 34 has a large area specific capacitance (5.4 $\mu F\ cm^{-2}$) and an ultra-high pressure response sensitivity (3.1 $nF\ kPa^{-1}$), which makes the thin film pressure sensor easy to perform pressure detection with a high sensitivity.

Figure 13:
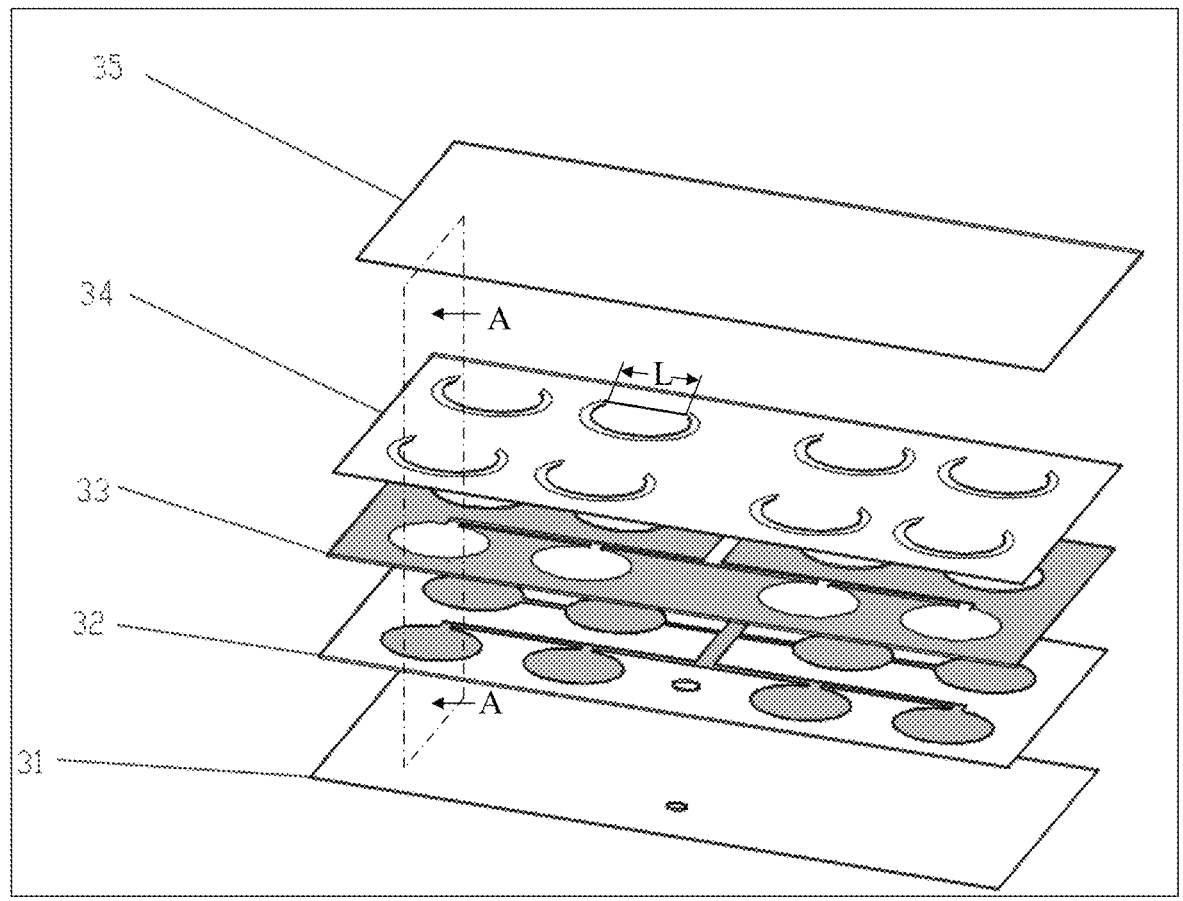
FIG. 13 is an exploded view of a second exemplar embodiment of the thin film pressure sensor, in accordance with aspects of the present invention.
Figure 14:
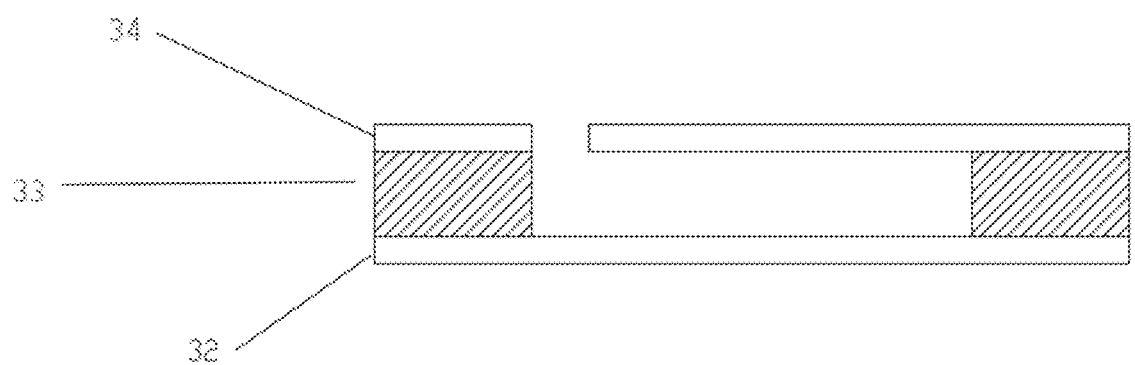
FIG. 14 is a sectional view taken along line A-A in FIG. 13 enlarging partially in a combined state.

Referring to FIGS. 13-14, corresponding to the thin film pressure sensor 3 in the second embodiment. The other parts of the thin film pressure sensor 3 are the same as the first embodiment. The difference is that: the functional film layer 34 is changed from a sealed type to a cantilever type, and a waterproof layer 35 is arranged outside the cantilever type functional film layer 34. The waterproof layer 35 is used for isolating the external water vapor to prevent the water vapor from entering the thin film pressure sensor 3. The waterproof layer 35 is made of a biocompatible material, and can be, for example, a latex rubber or silicone mold. The waterproof layer 35 can be bonded and sealed with the functional film layer 34 by a double-sided tape. At this point, the size of the waterproof layer 35 fits the functional film layer 34. In other embodiments, the waterproof layer 35 can also be used as a waterproof sleeve to seal the second end 12 of the capsule enclosure 1 and the thin film pressure sensor 3 as a whole, and seal the opening with a sealant, for example, epoxy sealant. The cantilever type functional film layer 34 is provided with a cantilever unit corresponding to the position of each sensing element 322, and the cantilever unit is cut in a functional film layer 34 of a preset shape, so that the functional film layer 34 forms a cantilever structure, as shown in FIG. 14. The preset shape can be a circle, an ellipse, a rectangle, etc., and the cut shape can be set as required, such as a circular ring (as shown in FIG. 14), a rectangle, etc. The cantilever chord length of the cantilever unit is 1-10 mm. As shown in FIG. 13, and the uncut chord length L of the cantilever is 1-10 mm. The cantilever type functional film layer 34 can reduce the curling stress of the thin film pressure sensor 3 curled to be affixed on the outer surface of the capsule enclosure 1, thereby enhancing the pressure detection performance of the thin film pressure sensor 3.

Figure 15:
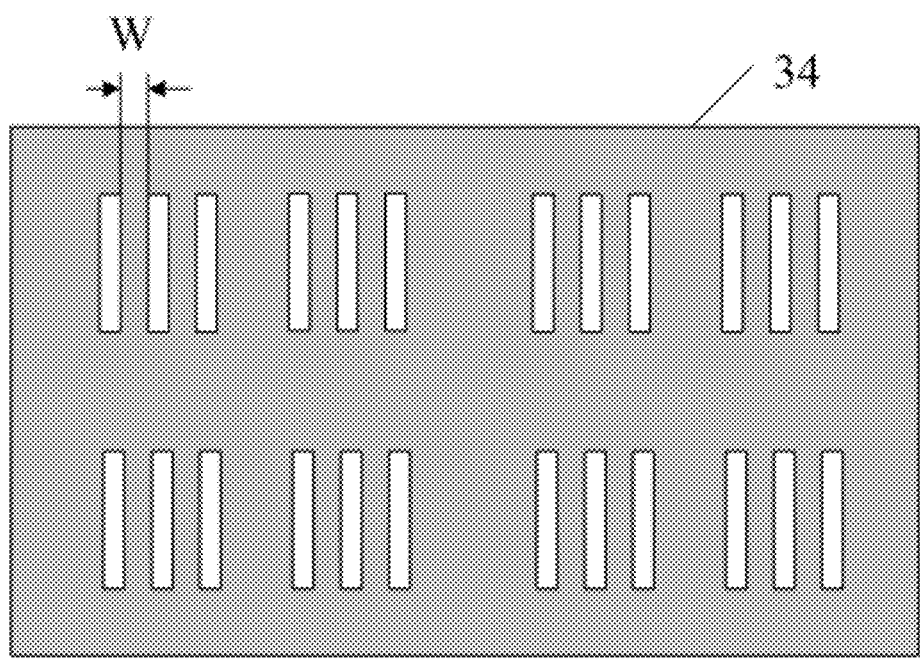
FIG. 15 is a schematic view of a third exemplar embodiment of a cantilever beam type functional film layer, in accordance with aspects of the present invention.

Of the thin film pressure sensor 3 in the third embodiment of the present invention, other parts are the same as the second embodiment, the difference is: the functional film layer 34 is changed from a cantilever type to a cantilever beam type, as shown in FIG. 15, a schematic diagram of a cantilever beam type functional film layer 34. The cantilever beam type functional film layer 34 is provided with a cantilever beam assembly corresponding to the position of each sensing element 322, and the cantilever beam assembly is cut in a functional film layer 34 of a preset shape, so that the functional film layer 34 forms a cantilever beam structure, as shown in FIG. 15. The preset shape can be a circle, an ellipse, a rectangle, etc., and the cut shape can be set as required, such as a rectangle, as shown in FIG. 15. Of the cantilever beam assembly, the cantilever width is 1-10 mm. As shown in FIG. 15, and the cantilever width W is 1-10 mm. The cantilever type functional film layer 34 can reduce the curling stress of the thin film pressure sensor 3 curled to be affixed on the outer surface of the capsule enclosure 1, thereby enhancing the pressure detection performance of the thin film pressure sensor 3, and the cantilever beam type functional film layer 34 has a better recovery effect than the cantilever type functional film layer 34 when pressure is reduced.

Figure 6:
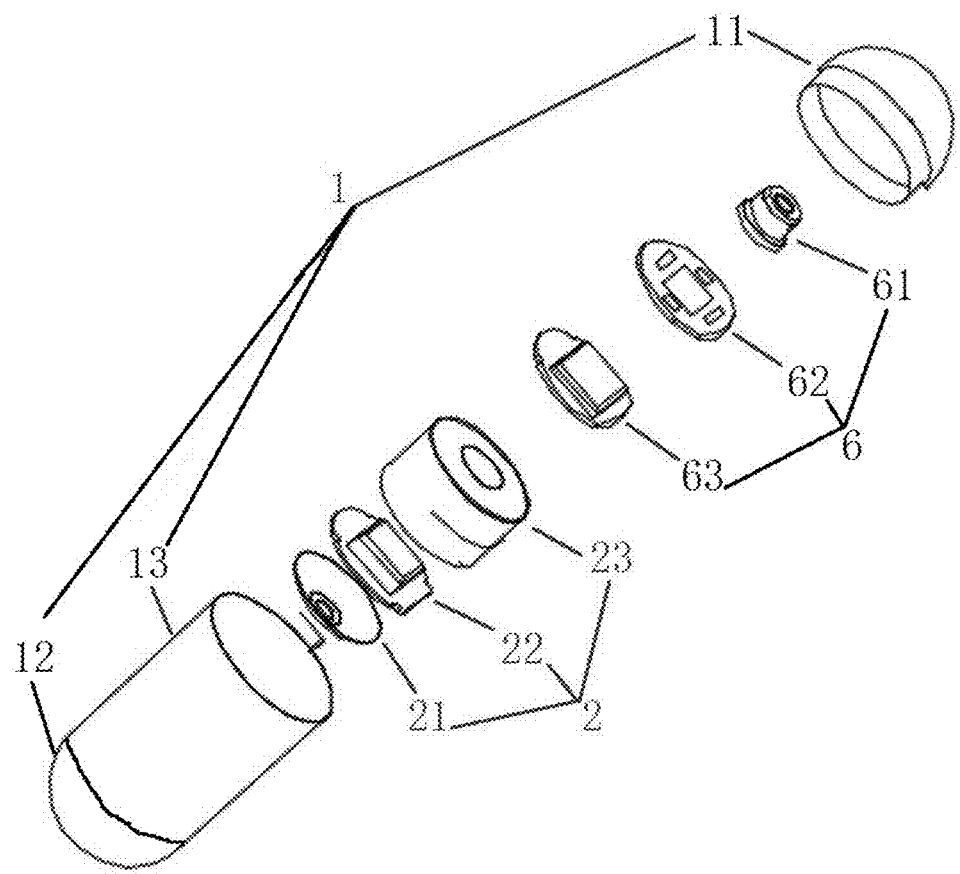
FIG. 6 is an exploded view of a capsule enclosure in FIG. 1.

Referring to FIG. 6, the capsule device further comprises an image acquisition assembly 6 for observing and taking images of the tissues in the subject. The image acquisition assembly 6 comprises a camera 61, an illuminating unit 62 and an image sensor 63. The data transmission assembly 2 comprises an antenna 21, a data collection and processing module 22, and a battery 23. The illuminating unit 62 comprises a plurality of LEDs. The second end 12 and the side wall 13 of the capsule are integrally formed. The antenna 21, the data collection and processing module 22, the battery 23, the image sensor 63, the illuminating unit 62 and the camera 61 are arranged in the accommodating chamber 10 in sequence from the second end 12 to the first end 11. The battery 23 is used to supply power to the data collection and processing module 22, the image sensor 63, the camera 61, and the illuminating unit 62, respectively, and the image sensor 63 is connected to the camera 61 and the data collection and processing module 22, respectively. In this way, the capsule device of the present application is actually a capsule endoscope, which can be used to explore the health conditions of the human intestines, stomach and esophagus.

In the present invention, the camera 61 is used to take images of tissue in the subject. The image sensor 63 can convert the optical signal of the tissue images into an electrical signal, and then the data collection and processing module 22 transmits the electrical signal to an external device through the antenna 21, thereby realizing an observation of the subject.

Figure 7:
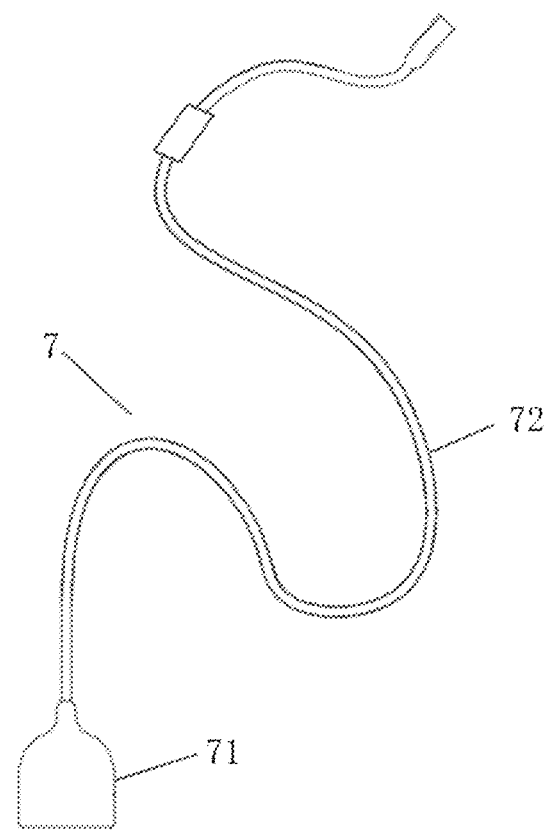
FIG. 7 is a structural view of an embodiment of a capsule tether, in accordance with aspects of the present invention.
Figure 8:
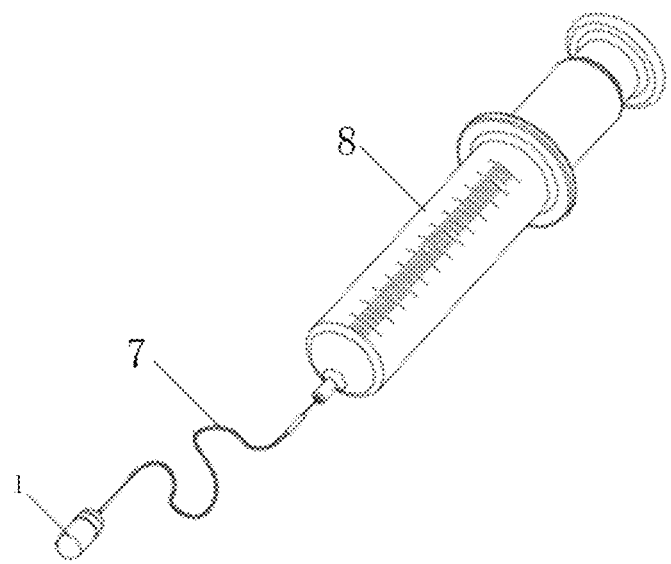
FIG. 8 is a schematic view of an embodiment of the connected capsule device, the capsule tether and a syringe.

Referring to FIG. 7 and FIG. 8, the capsule device further comprises a capsule tether 7 and an air source, and the air source can output air and generate corresponding force. In the embodiment, the air source is a syringe 8, while in other embodiments, the air source may also be an air injection pump, which has an air outlet. The two ends of the capsule tether 7 are connected to the syringe 8 and the capsule enclosure 1, respectively. Specifically, the capsule tether 7 comprises a suction cup 71 and a vent tube 72. One end of the vent tube 72 is connected to the air outlet of the syringe 8 so that the air output from the syringe 8 can enter the vent tube 72. The other end of the vent tube 72 is connected to the suction cup 71 and the suction cup 71 is used for connection with the capsule enclosure 1. The vent tube 72 can be a flexible tube that can be made of non-toxic materials with stable properties, such as biocompatible silicone, to ensure its safety. In addition, the outer diameter of the vent tube 72 can be set to 0.5-1.5 mm to ensure that the vent tube 72 does not produce too strong foreign body sensation in throat, and cannot cut the esophagus.

In an actual operation, the suction cup 71 is connected to the second end 12 of the capsule enclosure 1. After the capsule device connected to the capsule tether 7 is swallowed by a subject, according to the speed of the capsule device traveling downward in the esophagus, adjust the force of pulling the capsule enclosure 1 through the vent tube 72, and then realize repeated measurement and fixed-point measurement in the esophagus where objects travel down fast. After an examination is completed, push the piston rod of the syringe 8 forward to pump air to separate the suction cup 71 from the capsule enclosure 1.

The above are only preferred specific embodiments of the present invention, but the protection scope of the present invention is not limited to this. Any modifications or substitutions that can be readily thought of by any person skilled in the art within the technical scope disclosed by the present invention should be covered by the scope of protection of the present invention. Therefore, the scope of protection of the present invention should be subject to the scope of protection of the claims.

What is claimed is:

1. A capsule device for pressure measuring, comprises
a capsule enclosure,
a data transmission assembly and
a thin film pressure sensor;
    wherein
    the capsule enclosure is formed with an accommodating chamber;
    the data transmission assembly is arranged in the accommodating chamber; and
one or more thin film pressure sensors, attached to the outer surface of the capsule enclosure, each comprising
    a circuit layer,
    a bonding layer and
    a functional film layer, wherein
    the circuit layer and the functional film layer are bonded together through the bonding layer, and
    the circuit layer is attached to the outer surface of the capsule enclosure,
    wherein each thin film pressure sensor is connected with the data transmission assembly.

2. The capsule device of claim 1, wherein the capsule enclosure comprises
a cylindrical side wall, and
the thin film pressure sensor is attached to the outer surface of the side wall along the circumferential direction of the side wall.

3. The capsule device of claim 1, wherein the capsule device further comprises
a first vent passage, and wherein
    one end of the first vent passage is connected to the thin film pressure sensor, and
    the other end of the first vent passage is connected to the accommodating chamber.

4. The capsule device of claim 3, wherein the capsule device further comprises
a signal line, and wherein
one end of the signal line is connected to the thin film pressure sensor, and
the other end of the signal line is connected to the data transmission assembly.

5. The capsule device of claim 4, wherein
the signal line passes through the first vent passage.

6. The capsule device of claim 3, wherein
the first vent passage is arranged between the thin film pressure sensor and the capsule enclosure, and wherein
the capsule enclosure is arranged with an opening, and
the first vent passage is connected to the accommodating chamber via the opening.

7. The capsule device of claim 1, wherein the circuit layer comprises
a thin film,
one or more sensing elements are arranged on the thin film, and
one end of the signal line is connected to the sensing elements.

8. The capsule device of claim 7, wherein
a plurality of sensing elements is arranged on the thin film of the circuit layer,
wherein the sensing elements are arranged in an array, and
the sensing elements in each row are connected in series and
connected to the accommodating chamber through the signal line.

9. The capsule device of claim 7, wherein
the bonding layer is arranged with a first through hole to form a cavity between
the circuit layer and the functional film layer,
wherein
the cavity exposes all the sensing elements within the contact range of the functional film layer, and forms an air passage between the sensing elements and the accommodating chamber.

10. The capsule device of claim 9, wherein
the first through hole comprises a hole and a second vent passage, wherein the hole is arranged corresponding to the sensing element,
the sensing element is arranged in the hole, and
one end of the second vent passage is connected to the hole, and
the other end of the second vent passage is connected to the vent hole in the circuit layer.

11. The capsule device of claim 7, wherein the functional film layer comprises an iontronic film and a thin film, and the thin film is made of a biocompatible material.

12. The capsule device of claim 11, wherein
the functional film layer is of cantilever type,
a waterproof layer is arranged outside the cantilever type functional film layer, and
the waterproof layer is sealed and bonded to the cantilever type functional film layer.

13. The capsule device of claim 12, wherein
the cantilever type functional film layer is provided with a cantilever unit corresponding to the position of each sensing element, and
the cantilever unit is cut in a functional film layer of a preset shape, so that the functional film layer forms a cantilever structure.

14. The capsule device of claim 11, wherein
the functional film layer is of cantilever beam type,
a waterproof layer is arranged outside the cantilever beam type functional film layer, and the waterproof layer is sealed and bonded to the cantilever beam type functional film layer.

15. The capsule device of claim 14, wherein
the cantilever beam type functional film layer is provided with a cantilever beam assembly corresponding to the position of each sensing element, and the cantilever beam assembly is cut in a functional film layer of a preset shape, so that the functional film layer forms a cantilever beam structure.

16. The capsule device of claim 1, wherein the capsule device further comprises
an image acquisition assembly arranged in the accommodating chamber.

* * * * *